United States Patent
Bay et al.

(10) Patent No.: US 7,262,325 B2
(45) Date of Patent: Aug. 28, 2007

(54) METHOD OF PREPARING SALICYLAMIDES

(75) Inventors: William E. Bay, Ridgefield, CT (US); JoAnne P. Corvino, Harrison, NY (US)

(73) Assignee: Emisphere Technologies, Inc., Tarrytown, NY (US)

( * ) Notice: Subject to any disclaimer, the term of this patent is extended or adjusted under 35 U.S.C. 154(b) by 197 days.

(21) Appl. No.: 10/297,156

(22) PCT Filed: Jun. 4, 2001

(86) PCT No.: PCT/US01/18118

§ 371 (c)(1),
(2), (4) Date: Dec. 2, 2002

(87) PCT Pub. No.: WO01/92206

PCT Pub. Date: Dec. 6, 2001

(65) Prior Publication Data

US 2003/0216593 A1     Nov. 20, 2003

Related U.S. Application Data

(60) Provisional application No. 60/209,039, filed on Jun. 2, 2000.

(51) Int. Cl.
*C07C 231/02* (2006.01)
*C07C 233/65* (2006.01)

(52) U.S. Cl. ............... 564/134; 564/170; 560/103

(58) Field of Classification Search ............ 564/134, 564/170; 560/103
See application file for complete search history.

(56) References Cited

U.S. PATENT DOCUMENTS

| 2,835,668 | A |   | 5/1958 | Shapiro et al. ............ 260/244 |
| 3,907,893 | A | * | 9/1975 | Parker ..................... 564/135 |
| 4,379,928 | A | * | 4/1983 | Theodoropulos ........... 544/176 |
| 4,795,832 | A |   | 1/1989 | Leinen et al. .............. 564/134 |
| 5,442,092 | A |   | 8/1995 | Chopdekar et al. ......... 560/65 |
| 5,773,647 | A |   | 6/1998 | Leone-Bay et al. ......... 562/444 |
| 6,399,798 | B2 | * | 6/2002 | Gschneidner et al. ....... 554/35 |

FOREIGN PATENT DOCUMENTS

| GB | 1069367 | 5/1967 |
| WO | 9710197 | 3/1997 |
| WO | 0040539 | 7/2000 |
| WO | 0046182 | 8/2000 |
| WO | 0170219 | 9/2001 |

OTHER PUBLICATIONS

P. A. Brownsort and R. M. Patton, "Nitrile Sulphides. Part 7. Synthesis of [1]Benzopyrano[4,3-c]isothiazoles and isothiazolo[4,3-c]quinolines" J. Chem. Soc. Perkin Trans. vol. 11, 1987, pp. 2339-2344, esp. 2342.

M. N. Hossain and N. Borthakur, "O,O-Diethyldithiophosphoric acid—A new condensing agent for acylation of amines by carboxylic acid" Indian Journal of Chemistry, vol. 29B, Nov. 1990, pp. 1062-1063.

F. Palagiano et al., "Synthesis, stability and anticonvulsant activity of two new GABA prodrugs" Pharmazie, vol. 52, 1997, pp. 272-276.

* cited by examiner

*Primary Examiner*—Shailendra Kumar
(74) *Attorney, Agent, or Firm*—Darby & Darby

(57) ABSTRACT

The present invention provides a fast, high yield method for preparing salicylamide intermediates. The method comprises reacting a $C_4$ or higher alkyl ester of salicylic acid or derivative thereof with at least one amine selected from the group consisting of monoalkylamines, dialkylamines, ammonia, and any combination of any of the foregoing in alcohol to yield the salicylamide. The $C_4$ or higher alkyl ester of salicylic acid or a derivative thereof is preferably prepared by reacting salicylic acid or a derivative thereof with a $C_4$ or higher alcohol in presence of at least one of sulfuric acid, a sulfonic acid, and a mineral acid. This process for preparing salicylamide intermediates from salicylic acid or derivative thereof generally has a cycle time of about 2 days, and yields about 95% of a 99% pure material. In comparison, when a $C_3$ or lower alkyl ester is used in lieu of the $C_4$ or higher alkyl ester, the process generally has a cycle time of 7–9 days and yields about 60% of a 95% pure material. Methods of preparing an alkylated salicylamide are also provided.

13 Claims, No Drawings

METHOD OF PREPARING SALICYLAMIDES

This application is a national phase of International Application No. PCT/US01/18118, filed Jun. 4, 2001, which was published in English as WO 01/92206 and claims the benefit of U.S. Provisional Application No. 60/209,039, filed on Jun. 2, 2000, which is hereby incorporated by reference.

FIELD OF THE INVENTION

The present invention relates to methods of preparing salicylamide intermediates, $C_4$ or higher alkyl esters of salicylic acid and derivatives thereof, and alkylated salicylamides.

BACKGROUND OF THE INVENTION

U.S. Pat. Nos. 5,773,647 and 5,866,536 disclose compositions for the oral delivery of active agents, such as heparin and calcitonin, with modified amino acids, such as N-(5-chlorosalicyloyl)-8-aminocaprylic acid (5-CNAC), sodium N-(10-[2-hydroxybenzoyl]amino)decanoic acid (SNAD), and sodium N-(8-[2-hydroxybenzoyl]amino)caprylic acid (SNAC).

There is a need for a fast and efficient method for preparing salicylamides and alkylated salicylamides from salicylic acid and derivatives thereof.

SUMMARY OF THE INVENTION

The present invention provides a fast, high yield method for preparing salicylamide intermediates. The method comprises reacting a $C_4$ or higher alkyl ester of salicylic acid or a derivative thereof with at least one amine selected from the group consisting of monoalkylamines, dialkylamines, ammonia, and any combination of any of the foregoing in alcohol to yield the salicylamide.

The $C_4$ or higher alkyl ester of salicylic acid or a derivative thereof is preferably prepared by reacting salicylic acid or a derivative thereof with a $C_4$ or higher alcohol in the presence of at least one of sulfuric acid, a sulfonic acid, and a mineral acid. (i.e., an inorganic acid). This process for preparing salicylamide intermediates from salicylic acid or a derivative thereof generally has a cycle time of about 2 days, and yields about 95% of a 99% pure material. In comparison, when a $C_3$ or lower alkyl ester is used in lieu of the $C_4$ or higher alkyl ester, the process generally has a cycle time of 7–9 days and yields about 60% of a 95% pure material.

Yet another embodiment is a method of preparing an alkylated salicylamide comprising (a) reacting a $C_4$ or higher alkyl ester of salicylic acid or a derivative thereof with at least one amine selected from the group consisting of monoalkylamines, dialkylamines, ammonia, and any combination of any of the foregoing in alcohol to yield a first salicylamide; and (b) alkylating the first salicylamide to form the alkylated salicylamide.

Yet another embodiment is a method of preparing an alkylated salicylamide comprising (a) reacting salicylic acid or a derivative thereof with a $C_4$ or higher alcohol in the presence of at least one of sulfuric acid, a sulfonic acid and a mineral acid to form a $C_4$ or higher alkyl ester of salicylic acid or a derivative thereof; (b) converting the $C_4$ or higher alkyl ester into a first salicylamide; and (c) alkylating the first salicylamide to form the alkylated salicylamide.

DETAILED DESCRIPTION OF THE INVENTION

The present invention provides a fast, high yield method for preparing salicylamide intermediates. As a result, the cycle time for preparing alkylated salicylamides, such as 5-CNAC, via this intermediate is drastically reduced.

The terms "alkyl", "alkenyl", and "alkynyl" as used herein include linear and branched alkyl, alkenyl, and alkynyl substituents, respectively.

Preparation of $C_4$ or Higher Alkyl Esters of Salicylic Acid and Derivatives Thereof The $C_4$ or higher alkyl ester may be prepared by reacting salicylic acid or a derivative thereof with a $C_4$ or higher alcohol in the presence of at least one of sulfuric acid, a sulfonic acid, and a mineral acid.

According to one embodiment, the salicylic acid or derivative thereof has the formula

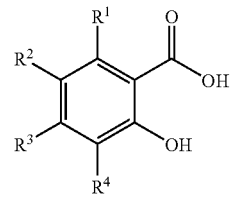

where $R^1$, $R^2$, $R^3$, and $R^4$ are independently hydrogen, —OH, —O—$R^5$, substituted or unsubstituted alkyl, substituted or unsubstituted alkenyl, substituted or unsubstituted alkoxy, substituted or unsubstituted aryl, carboxy, substituted or unsubstituted alkoxycarbonyl, halogen, nitrile, —OC(O)CH$_3$, —SO$_3$H, or —NR$^6$R$^7$;

$R^5$ is hydrogen, alkyl, or aryl; and $R^6$ and $R^7$ are independently hydrogen, $C_1$–$C_4$ alkyl, or oxygen.

The alkyl, alkenyl, alkoxy and aryl groups of $R^1$, $R^2$, $R^3$, $R^4$, and $R^5$ may be substituted with, for example, —OH, F, and alkyl and aryl groups. $R^1$, $R^2$, $R^3$, $R^4$, and $R^5$ may be $C_1$–$C_{18}$ alkyl, $C_2$–$C_{18}$ alkenyl, or $C_1$–$C_{18}$ alkoxy. In particular, $R^1$, $R^2$, $R^3$, $R^4$, and $R^5$ may be $C_1$–$C_4$ alkyl, $C_2$–$C_4$ alkenyl, or $C_1$–$C_4$ alkoxy. The alkoxycarbonyl group of $R^1$, $R^2$, $R^3$, $R^4$, and $R^5$ may be substituted with, for example, alkyl groups.

Preferred halogens for $R^1$, $R^2$, $R^3$, and $R^4$ are chlorine, bromine, and fluorine. Preferred alkyl groups for $R^1$, $R^2$, $R^3$, and $R^4$ include, but are not limited to, methyl and ethyl. Preferred alkoxy groups for $R^1$, $R^2$, $R^3$, and $R^4$ include, but are not limited to, methoxy and ethoxy.

According to one preferred embodiment, $R^1$, $R^2$, $R^3$, and $R^4$ are independently hydrogen, methoxy, or chlorine. According to a more preferred embodiment, $R^1$, $R^2$, $R^3$, and $R^4$ are hydrogen. According to another more preferred embodiment, $R^1$, $R^3$, and $R^4$ are hydrogen and $R^2$ is chlorine. According to yet another embodiment, $R^1$, $R^2$, and $R^4$ are hydrogen and $R^3$ is methoxy.

Suitable alcohols include those that form two-phase azeotropes. Examples of such alcohols include, but are not limited to, linear and branched primary alcohols. Preferred alcohols include, but are not limited to, linear and branched $C_4$–$C_8$ alcohols (i.e. butanol, pentanol, hexanol, heptanol, and octanol). A more preferred alcohol is n-butanol. Since propanol and lower alcohols do not form two-phase azeotropes, reactions with these alcohols produce solutions in which the ester product is difficult to separate from the water by-product.

A non-limiting example of a suitable sulfonic acid is p-toluene sulfonic acid. Suitable mineral acids include, but are not limited to, hydrochloric acid, hydrogen bromide, phosphoric acid, and any combination of any of the foregoing.

Generally, the reaction mixture includes a molar excess of $C_4$ or higher alcohol relative to salicylic acid or derivative thereof. The reaction mixture broadly includes from about 2% by weight to the saturation concentration of salicylic acid or derivative thereof, based on 100% weight of reaction mixture. Generally, from about 1 to 30% by weight of at least one of sulfuric acid, a sulfonic acid, and a mineral acid is included in the reaction mixture, based on 100% weight of reaction mixture. According to one embodiment, the reaction mixture includes from about 5 to about 15% by weight of at least one of sulfuric acid, a sulfonic acid, and a mineral acid, based on 100% weight of reaction mixture.

This reaction is typically performed at a temperature of from about 90 to about 120° C. and preferably at from about 95 to about 117° C. Generally, this reaction is performed at a pressure of from about 0.8 to about 2.0 atm and preferably at from about 0.95 to about 1.05 atm. According to a preferred embodiment, this reaction is performed under a dry nitrogen ($N_2$) blanket.

Water is preferably removed during or after formation of the $C_4$ or higher alkyl ester. More preferably, water is removed during the reaction, such as by azeotropic removal.

This method can produce $C_4$ or higher alkyl esters of salicylic acid and derivatives having the formula:

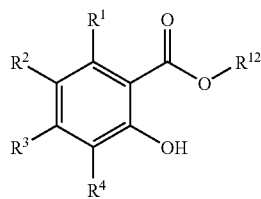

where
$R^1$, $R^2$, $R^3$, and $R^4$ are defined as above; and
$R^{12}$ is a linear or branched $C_4$ or higher alkyl.

Preferably, $R^{12}$ is a linear or branched $C_4$–$C_8$ alkyl and more preferably $R^{12}$ is n-butyl.

Preparation of Salicylamide from $C_4$ or Higher Alkyl Esters of Salicylic Acid and Derivatives Thereof The $C_4$ or higher alkyl ester of salicylic acid or derivative thereof is reacted with at least one amine selected from the group consisting of monoalkylamines, dialkylamines, ammonia, and any combination of any of the foregoing in alcohol to yield the (unprotected and unactivated) salicylamide. The $C_4$ or higher alkyl ester is preferably a $C_4$–$C_8$ alkyl ester and more preferably a butyl ester, such as an n-butyl ester.

Suitable alcohols include, but are not limited to, $C_1$–$C_4$ alcohols, such as methanol, ethanol, and propanol; glycols, such as ethylene glycol; and any combination of any of the foregoing. A preferred alcohol is methanol. Since methanol has the greatest solubility for ammonia of all the alcohols, it promotes the reaction more than any other alcohol when ammonia is used.

Suitable monoalkylamines include, but are not limited to, monomethylamine, monoethylamine, and any combination of any of the foregoing. Suitable dialkylamines include, but are not limited to, dimethylamine, diethylamine, and any combination of any of the foregoing. According to one preferred embodiment, the amine is ammonia and more preferably anhydrous ammonia.

Generally, the reaction mixture contains a molar excess of amine relative to the alkyl ester. The molar ratio of amine to alkyl ester preferably ranges from about 5:1 to about 50:1 and more preferably from about 5:1 to about 15:1.

When water is present, the reaction slows down and the ester can be hydrolyzed back to the starting salicylic acid or derivative thereof. Accordingly, the reaction is preferably performed in an environment substantially free of water and more preferably in an environment having less than about 1% by weight of water (based on 100% weight or reaction mixture). For example, the reaction may be performed under a dry nitrogen ($N_2$) or ammonia ($NH_3$) blanket. Preferably, the ammonia and methanol are applied under anhydrous conditions.

The reaction is typically performed at a temperature of from about 25 to about 80° C. and preferably at from about 35 to about 50° C. Generally, the reaction is performed at a pressure of from about 1 to about 10 atm and preferably at from about 2 to about 3 atm.

Salicylamide intermediates which may be prepared by this method include, but are not limited to, those having the formula

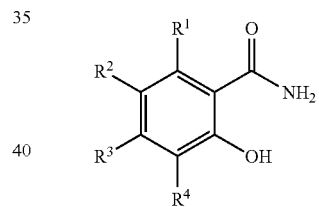

where $R^1$, $R^2$, $R^3$, and $R^4$ are defined as above. Special mention is made of 5-chlorosalicylamide and 4-methoxy salicylamide.

The salicylamide intermediate may be purified by any method known in the art. For example, it may be purified by recrystallization or by fractionation on one or more solid chromatographic supports, alone or linked in tandem. Suitable recrystallization solvent systems include, but are not limited to, acetonitrile, methanol, and tetrahydrofuran. Fractionation may be performed on a suitable chromatographic support such as alumina, using methanol/n-propanol mixtures as the mobile phase; reverse phase chromatography using trifluoroacetic acid/acetonitrile mixtures as the mobile phase; and ion exchange chromatography using water or an appropriate buffer as the mobile phase. When anion exchange chromatography is performed, preferably a 0–500 mM sodium chloride gradient is employed.

Preparation of Alkylated Salicylamides

Alkylated salicylamides, such as 5-CNAC, may be prepared from the salicylamide intermediates of the present invention, such as by the methods described in International Publication No. WO 00/46182 and International Patent Application No. PCT/US01/09154, both of which are hereby incorporated by reference. Generally, the unprotected and unactivated (unprotected/unactivated) salicylamide intermediate is alkylated to form the alkylated salicylamide. One preferred method of alkylating the salicylamide intermediate is by (i) protecting and activating the unprotected/unactivated salicylamide to form a protected and activated (protected/activated) salicylamide; (ii) alkylating the protected/activated salicylamide with an alkylating agent to form a protected/activated alkylated salicylamide; and (iii) deprotecting and deactivating the protected/activated alkylated salicylamide to form the alkylated salicylamide.

The term "protected salicylamide" is defined herein as a salicylamide where the hydroxy moiety of the salicyl group has been protected to prevent reaction of the hydroxy moiety. The term "activated salicylamide" is defined herein as a salicylamide where the nitrogen atom of the amide group has been activated so that the nitrogen atom is in a more reactive condition, i.e., more prone to reaction.

Suitable protected/activated salicylamides include, but are not limited to, compounds having the formula

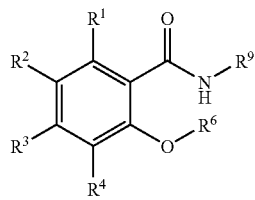

where
$R^1$, $R^2$, $R^3$, and $R^4$ are defined as above;
$R^8$ is a protecting group;
$R^9$ is an activating group; or
$R^8$ and $R^9$ are combined to form a cyclic group, i.e., $R^8$ and $R^9$ form a single group that forms a heterocycle with the oxygen atom and nitrogen atom of the amide moiety. For example, carsalam, which has the formula

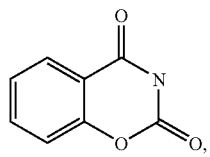

is a suitable protected/activated salicylamide.

The protecting and activating groups may be the same or different. The protecting and activating groups may be separate moieties (each attached to one of the hydroxy or amide moieties) or a single moiety (attached to both the hydroxy and amide moieties).

Suitable protecting groups include, but are not limited to, —C(O)CH$_3$; —C(O)F$_3$; —S(O)$_2$CH$_3$; —S(O)$_2$CF$_3$; benzyl; silyl; tetrahydropyranyl; and methylenealkoxy, such as methylenemethoxy and methyleneethoxy. Suitable activating groups include, but are not limited to, —C(O)CH$_3$; —C(O)CF$_3$; —S(O)$_2$CH$_3$; and —S(O)$_2$CF$_3$. Preferably, $R^8$ and $R^9$ are combined to form a cyclic group which protects the hydroxy moiety and activates the nitrogen atom of the amide moiety. More preferably, combined $R^8$ and $R^9$ are —C(O)— or —S(O)$_2$—.

Preferred protected/activated salicylamides include, but are not limited to, carsalam and derivatives thereof having the formula

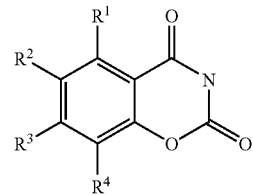

where $R^1$, $R^2$, $R^3$, and $R^4$ are defined as above.

One method of preparing the protected/activated salicylamide of the present invention comprises protecting the hydroxy moiety of the salicylamide intermediate and activating the amide moiety of the salicylamide intermediate. The protecting and activating steps may be performed in any order, but are preferably performed simultaneously. For example, the protecting step may be performed before performing the activating step.

The hydroxy moiety of the salicylamide intermediate may be protected by methods known in the art. For example, the hydroxy moiety may be protected by reacting the salicylamide with a protecting agent, such as an activated halide. The resulting salicylamide has a protecting group attached to the oxygen atom of the hydroxy moiety. Examples of activated halides include, but are not limited to, acyl halides; silyl halides, such as silyl chlorides; benzyl halides; and methylene alkoxy halides, such as methylene methoxy halides and methylene ethoxy halides. Preferably, the reaction with an activated halide is performed in the presence of a base, such as potassium carbonate, triethylamine, or pyridine.

Another example of a protecting agent is an activated ether. Examples of activated ethers include, but are not limited to, dihydropyranyl ether. Preferably, the activated ether is reacted with the salicylamide under acid catalysis conditions, such as with sulfuric acid, para-toluene sulfonic acid, or camphor sulfonic acid in methylene chloride, tetrahydrofuran, or toluene.

The amide moiety of the salicylamide intermediate may be activated by methods known in the art. For example, the amide moiety may be activated by reacting the salicylamide with an activating agent, such as an acyl halide, acyl anhydride, sulfonyl halide, or sulfonyl anhydride. The resulting salicylamide has an activating group attached to the nitrogen atom of the amide moiety. Suitable acyl halides include, but are not limited to, those described above for protecting the hydroxy moiety of the salicylamide. Preferably, the activating agent is reacted with the salicylamide in the presence of a base, such as potassium carbonate, triethylamine, or pyridine.

In the preparation of carsalam and the aforementioned derivatives thereof, the protecting and activating steps are typically performed simultaneously and the protecting and activating groups are a single group attached to both the hydroxy and amide moieties. One method of preparing carsalam and the derivatives thereof is by reacting the corresponding (unprotected and unactivated) salicylamide with an alkyl chloroformate, such as ethyl chloroformate; a phenyl chloroformate; or an imidazole alkoxy carbonyl.

The protected/activated salicylamide may be alkylated by the methods known in the art for alkylating phthalimide to form a primary amine. See, for example, Gibson and Bradshaw, *Angewandte Chemie*, International Edition in English, 7:919–930 (1968). The protected/activated salicylamide is substituted for the phthalimide in these methods.

The protected/activated salicylamide may also be alkylated by reacting the protected/activated salicylamide with an alkylating agent. The alkylating agent reacts with the nitrogen atom of the amide moiety of the salicylamide. The alkylating agent may be any known in the art, such as compounds of the formula $$X-R^{10}-R^{11}$$

where $R^{10}$ is a linear or branched, $C_1$–$C_{20}$ alkylene, alkenylene, or alkynylene;

$R^{10}$ is optionally substituted with $C_1$–$C_4$ alkyl, $C_1$–$C_4$ alkenyl, oxygen, nitrogen, sulfur, halogen, —OH, $C_1$–$C_4$ alkoxy, aryl, heteroaryl, or vinyl;

$R^{10}$ is optionally interrupted with aryl, heteroaryl, vinyl, oxygen, nitrogen, or sulfur;

$R^{11}$ is carboxyl or a salt thereof, carboxylate, nitrile, halogen, ester, amine or salt thereof, alcohol, or thiol; and X is a suitable leaving group. Suitable leaving groups include, but are not limited to, halogens, such as chlorine, bromine, and iodine, and alcohols. Preferred alcohols include, but are not limited to, activated alcohols. Two preferred leaving groups are chlorine and bromine.

$R^{10}$ may be substituted with an alkoxy moiety, such as methoxy or ethoxy. Preferably, $R^{10}$ is —$(CH_2)_n$— where n is an integer from 1 to 12, more preferably from 7 to 9, and most preferably 7.

$R^{11}$ is preferably a carboxyl or a salt thereof. Salts include, but are not limited to, organic and inorganic salts, for example, alkali-metal salts, such as sodium, potassium and lithium; alkaline-earth metal salts, such as magnesium, calcium or barium; ammonium salts; basic amino acids, such as lysine and arginine; and organic amines, such as dimethylamine and pyridine. More preferably, $R^{11}$ is a sodium salt of carboxyl.

In a preferred embodiment, $R^1$, $R^2$, $R^3$, and $R^4$ of the protected/activated salicylamide are hydrogen and $R^{10}$ of the alkylating agent is —$(CH_2)_7$— or —$(CH_2)_9$—. According to another preferred embodiment, $R^1$, $R^2$, and $R^4$ of the protected/activated salicylamide are hydrogen, $R^2$ is chlorine, and $R^{10}$ of the alkylating agent is —$(CH_2)_3$— or —$(CH_2)_7$—. According to yet another preferred embodiment, $R^1$, $R^3$, and $R^4$ of the protected/activated salicylamide are hydrogen, $R^3$ is methoxy, and $R^{10}$ of the alkylating agent is —$(CH_2)_7$—.

Other suitable alkylating agents include, but are not limited to, dicarboxylate alkylating agents, such as those having the formula

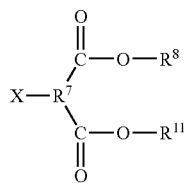

where $R^7$ is a linear or branched, $C_1$–$C_{20}$ alkylene, alkenylene, or alkynylene;

$R^7$ is optionally substituted with $C_1$–$C_4$ alkyl, $C_1$–$C_4$ alkenyl, oxygen, nitrogen, sulfur, halogen, —OH, $C_1$–$C_4$ alkoxy, aryl, heteroaryl, or vinyl;

$R^7$ is optionally interrupted with aryl, heteroaryl, vinyl, oxygen, nitrogen, or sulfur;

$R^8$ and $R^{11}$ are independently $C_1$–$C_4$ alkyl or $C_1$–$C_4$ haloalkyl; and X is a suitable leaving group.

Suitable leaving groups include, but are not limited to, halogens and alcohols. Two preferred leaving groups are chlorine and bromine. Preferably, $R^8$ and $R^{11}$ are independently $C_1$–$C_4$ alkyl. Preferably, $R^8$ and $R^{11}$ are the same. $R^7$ is preferably $C_4$–$C_{12}$ alkylene and more preferably $C_7$–$C_9$ alkylene.

A preferred dicarboxylate alkylating agent has the formula

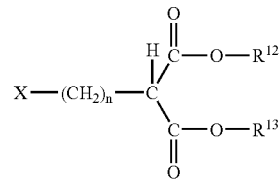

where $R^{12}$ and $R^{13}$ are independently $C_1$–$C_4$ alkyl;

X is a suitable leaving group; and n is an integer from 2 to 12.

Preferably, n ranges from 3 to 10, more preferably from 4 to 8, and most preferably from 6 to 8. Non-limiting examples of dicarboxylate alkylating agents include 2-(6-bromohexyl)-malonic acid diethyl ester and 2-(8-bromooctyl)malonic acid diethyl ester, which are available from Allied Signal, Inc. of Morristown, N.J.

The reaction between the alkylating agent and the protected/activated salicylamide is preferably carried out in the presence of a slight molar excess of protected/activated salicylamide relative to alkylating agent. Generally, the molar ratio of protected/activated salicylamide to alkylating agent ranges from about 1:1 to about 1:0.5, preferably from about 1:0.8 to about 1:0.99, and most preferably about 1:0.95.

The alkylating reaction is preferably performed in the presence of a suitable base, such as pyridine, picoline, tetramethylguanidine, triethylamine, diisopropylethylamine, sodium or potassium bicarbonate, sodium or potassium carbonate, or any combination of any of the foregoing. According to a preferred embodiment, the base is sodium carbonate. Generally, the reaction is performed in the presence of a slight molar excess of base relative to the protected/activated salicylamide.

The reaction may be carried out in solvents including, but not limited to, dimethylacetamide (DMAC); dimethylformamide (DMF); ketones, such as acetone, methylethylketone, and methylisobutylketone; and any combination of any of the foregoing. Preferably, the solvent is non-aqueous.

The alkylating reaction is generally performed at a temperature of from about 20 to about 100° C. The reaction is preferably performed at a temperature of from about 40 to about 80° C., from about 50 to about 80° C., or from about 60 to about 80° C. Most preferably, the alkylating reaction is performed at about 70° C. The reaction is typically performed at atmospheric pressure to full vacuum and preferably from about 22 to about 2441 Hg of vacuum.

The reaction mixture prior and during the alkylating reaction preferably contains less than 5%, more preferably less than 3%, and most preferably less than 1% by weight of water, based upon 100% total weight of reaction mixture.

The reaction is generally performed for a time sufficient to ensure the complete reaction of the protected/activated salicylamide. The reaction duration varies depending on the starting materials. Generally, the reaction is allowed to run for a time sufficient so that at least about 90% and preferably 99% of the limiting reagent, i.e., the alkylating agent, has been consumed, but is stopped before significant side reaction product build up. This reduces or eliminates the need for purification of the final product. Preferably, it is performed for from about 2 to about 18 hours, more preferably from about 3 to about 5 hours, and most preferably about 4 hours.

Carsalam and carsalam derivatives are preferably alkylated in the presence of a slight molar excess of base. A preferred base for such an alkylation reaction is sodium carbonate. A molar excess of sodium carbonate relative to carsalam or carsalam derivative is generally used. More preferably, the carsalam or the carsalam derivative is alkylated by sequentially adding sodium carbonate to a solvent, such as those described above (e.g. DMAC); adding carsalam or the carsalam derivative to the solution; and adding a dicarboxylate alkylating agent to the solution. The alkylating agent is preferably added to the solution immediately following the addition of carsalam or carsalam derivative and more preferably within about 10 seconds after the completion of the carsalam or carsalam derivative addition. When the base, in this case sodium carbonate, is reacted with the carsalam or carsalam derivative, carsalam-sodium or carsalam derivative-sodium and sodium bicarbonate are formed. While carsalam has a solubility of about 30% in DMAC, carsalam-sodium only has a solubility of about 6% in DMAC. Sodium bicarbonate can react with the carsalam or carsalam derivative resulting in the formation of carbonic acid, which may further react to form water. Generally, water significantly reduces the efficacy of the alkylating agent. In order to minimize the reaction of sodium bicarbonate with the carsalam or carsalam derivative, the carsalam or carsalam derivative is preferably reacted with a molar excess of sodium carbonate. The water content of the reaction mixture may also be reduced by performing the reaction in a low pressure atmosphere (e.g a vacuum).

According to another embodiment, the carsalam-sodium or carsalam derivative-sodium is isolated prior to being reacted with the alkylating agent in order to reduce water content.

The alkylation reaction may be performed with alcohols under Mitsunobu conditions. See Mitsunobu, W. and Sano, J., *J. Amer. Chem. Soc.*, 94:674 (1972). Such alkylation reactions are performed in the presence of triphenylphosphene (PPh$_3$) and dialkyl azodicarboxylates, such as diisopropyl azodicarboxylate (DIAD). The products of this reaction may be hydrolyzed to the corresponding alkylated salicylamides.

The protected/activated alkylated salicylamide is then (a) deprotected and deactivated, (b) optionally, hydrolyzed, and (c) optionally, decarboxylated (when alkylated with a dicarboxylate alkylating agent) to yield the alkylated salicylamide. Typically, these steps entail the removal of the protecting and activating groups from the salicylamide. The decarboxylate step entails removal of a carboxylate moiety from the alkylated salicylamide. The protecting and activating groups may be removed by acidic, basic and/or neutral hydrolysis as known in the art.

When alkylated with a dicarboxylate alkylating agent, the carboxylate moiety or moieties of the alkylated salicylamide may optionally be hydrolyzed to form a carboxylic acid moiety or carboxylic acid moieties or carboxylate salt. The protecting and activating groups and one of the carboxylate groups may be removed and the remaining carboxylate group may be hydrolyzed by acidic, basic and/or neutral hydrolysis as known in the art.

Neutral hydrolysis may be performed, for example, with super-heated water at a temperature of from about 100 to about 250° C.

Deprotection

The salicylamide may be deprotected by any method known in the art, such as acidic, basic, or neutral hydrolysis. Deprotection is preferably performed by basic hydrolysis. Basic hydrolysis may be performed, for example, with aqueous sodium carbonate or aqueous sodium hydroxide. According to one embodiment, basic hydrolysis is performed with aqueous sodium hydroxide at a temperature of from about 78 to about 98° C.

Another method of deprotecting is by acidic hydrolysis. Acidic hydrolysis may be performed, for example, with aqueous hydrochloric acid or aqueous trifluoroacetic acid. For example, acidic hydrolysis may be performed with aqueous hydrochloric acid in acetone at a temperature of from about 25 to about 65° C. According to one embodiment, acidic hydrolysis is performed at a pH of about 3.5 to 4.5 and preferably at about 4. The acidic hydrolysis process may also deactivate the salicylamide.

Deactivation

The activating group may be removed by any method known in the art. When acidic or basic hydrolysis is performed to deprotect the salicylamide, the activating group may be removed by neutralization. For example, when deprotection is performed by basic hydrolysis, the salicylamide may be deactivated by adding an aqueous acid, such as hydrochloric acid or aqueous trifluoroacetic acid. When deprotection is performed by acidic hydrolysis, the salicylamide may be deactivated by adding an aqueous basic.

Hydrolysis

Optionally, the alkylated salicylamide may be further reacted to modify the end group(s) of the alkylating moiety as well as the oxygen group attached to the phenyl ring. For example, the end group —CN or —C(O)O—CH$_2$—CH$_3$ may be modified to —COOH or a salt thereof. This may be accomplished by methods known in the art, such as neutralization and acidic, basic, and neutral hydrolysis. Generally, hydrolysis of the salicylamide is performed by neutralizing the deprotected and deactivated salicylamide. When the salicylamide is deprotected by basic hydrolysis, the free acid of the salicylamide is, for example, recovered by neutralization with an aqueous acid, such as hydrochloric acid.

Decarboxylation

If a monocarboxylic salicylamide is desired and the salicylamide has been alkylated with a dicarboxylate alkylating agent, the prepared alkylated salicylamide may be decarboxylated. The decarboxylation step is performed either before or after the deprotecting and deactivating steps and optional hydrolysis step. Preferably, decarboxylation is performed after the deprotecting and deactivating steps and optional hydrolysis step.

The decarboxylation step removes one of the carboxylate moieties from the alkylated salicylamide. Decarboxylation can be performed by any method known in the art, such as acidic hydrolysis as discussed above. In order to control foaming due to the release of carbon dioxide, the reaction may be performed in the presence of acetone.

Decarboxylation can also be performed by heating the alkylated salicylamide in a high boiling point organic solvent, such as xylenes, toluene, heptane, dimethyl acetamide (DMA or DMAC), dimethyl formamide (DMF), methyl sulfoxide, isoparaffins (e.g. isopar-G, isopar-H, isopar-L, and isopar-K available from Exxon Chemicals of Houston, Tex.), and any combination of any of the foregoing. The organic solvent preferably has a boiling point of at least 110° C. and more preferably of at least 140° C. The decarboxylation reaction is preferably performed at a temperature ranging from about 140 to about 20° C. and more preferably ranging from about 140 to about 160° C. The temperature at which the reaction is performed should be sufficient to remove one of the carboxylate groups at the end of the added alkyl chain.

Preferably, any water in the reaction mixture is removed prior to heating. Water may be removed from a reaction mixture containing the free acid of the alkylated salicylamide (which is formed if the alkylated salicylamide is hydrolyzed as described in the "Hydrolysis" section above) as follows. The alkylated salicylamide is mixed with an organic solvent in which it is soluble, such as xylenes. The aqueous layer is then extracted, which in this case is the lower layer, leaving the alkylated salicylamide in xylenes. The reaction mixture may then be heated to decarboxylate the alkylated salicylamide.

The reaction mixture prior and during the decarboxylation reaction preferably contains less than 5%, more preferably less than 3%, and most preferably less than 1% by weight of water, based upon 100% total weight of reaction mixture.

The decarboxylation step may also be performed neat (i.e. without a solvent) by heating the deprotected, deactivated, and, optionally, hydrolyzed alkylated salicylamide to a temperature ranging from about 140 to about 200° C.

The deprotecting, deactivating, hydrolyzing, and decarboxylating steps may be performed at a temperature of from about 20 to about 200° C. According to one embodiment, the deprotecting and deactivating step is performed at a temperature of from about 20 to about 100° C. and preferably from about 90 to about 100° C.

Suitable solvents for the protected/activated alkylated salicylamide in the deprotecting, deactivating, decarboxylating, and hydrolyzing step include, but are not limited to, water, organic solvents, such as ethanol, dimethylacetamide (DMAC), dimethylformamide (DMF), ketones (e.g. acetone, methylethylketone, and methylisobutylketone), and any combination of any of the foregoing.

When the protected/activated salicylamide is carsalam or a derivative thereof, the alkylated salicylamide may be deprotected by hydrolysis, such as basic hydrolysis. This causes the bonds between the carbonyl group and the adjacent oxygen atoms to cleave, thereby deprotecting the hydroxyl moiety. Hydrolysis may be carried out under conditions known in the art.

After hydrolysis of-the carsalam or carsalam derivative, the activated salicylamide may be deactivated by methods known in the art. For example, hydrochloric acid may be added to the activated alkylated salicylamide until the pH of the reaction mixture is from about 3.5 to about 4.5 or until the pH is less than about 4. This causes the bond between the carbonyl moiety and the nitrogen atom of the amide moiety of the salicylamide to cleave and release carbon dioxide. The hydrochloric acid may also remove one of the carboxylate moieties and hydrolyze the remaining carboxylate moiety (when a dicarboxylate alkylating agent is used).

Alternatively, after hydrochloric acid is added to deactivate the alkylated salicylamide, the alkylated salicylamide can be decarboxylated by heating it in xylenes or other high boiling point organic solvent, such as those discussed above, to reflux or near reflux. For example, when xylene is used as the solvent, the mixture is preferably heated to a temperature ranging from about 105 to about 140° C.

Salts of the alkylated salicylamide may be formed by any method known in the art. For example, the acid form of the alkylated salicylamide, i.e., where the alkylated salicylamide has a —COOH moiety, may be converted into the corresponding sodium salt by reacting it with sodium hydroxide. Suitable salts include, but are not limited to, organic and inorganic salts, for example alkali-metal salts, such as sodium, potassium and lithium; alkaline-earth metal salts, such as magnesium, calcium or barium; ammonium salts; basic amino acids, such as lysine or arginine; and organic amines, such as dimethylamine or pyridine. Sodium salts include, but are not limited to, mono-, di-, and other multi-valent sodium salts. A preferred salt is the disodium salt. The salts may also be solvates, including ethanol solvates, and hydrates. The term "solvate" as used herein includes, but is not limited to, a molecular or ionic complex of molecules or ions of a solvent, such as ethanol, with ions or molecules of the compounds of the present invention.

Optionally, the alkylated salicylamide may be further reacted to modify the end group of the alkylating moiety. For example, the end group —CN or —C(O)O—CH$_2$—CH$_3$ may be modified to —COOH or a salt thereof. This may be accomplished by methods known in the art, such as acidic and basic hydrolysis.

The present method may be used to prepare alkylated salicylamides having the formula

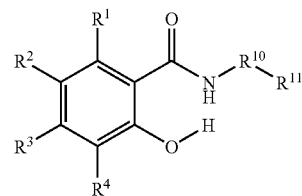

where $R^1$, $R^2$, $R^3$, $R^4$, $R^{10}$, and $R^{11}$ are defined as above. Special mention is made of N-(5-chlorosalicyloyl)-8-aminocaprylic acid, N-(10-[2-hydroxybenzoyl]amino)decanoic acid, N-(8-[2-hydroxybenzoyl]amino)caprylic acid, N-(4-methoxysalicyloyl)-8-aminocaprylic acid, and their salts, including, but not limited to, sodium salts (such as their monosodium and disodium salts).

The alkylated salicylamides of the present invention may be purified by recrystallization or fractionation on one or more chromatographic supports. Fractionation may be performed on suitable chromatographic supports, such as silica gel or alumina, using solvent mixtures such as acetic acid/butanol/water as the mobile phase; reverse phase column supports using trifluoroacetic acid/acetonitrile mixtures as the mobile phase; and ion exchange chromatography using water as the mobile phase. The alkylated salicylamides may also be purified to remove impurities, such as inorganic salts, by extraction with a lower alcohol, such as methanol, butanol, or isopropanol.

The method of the present invention uses readily available and inexpensive starting materials and provides a cost-effective method for preparing and isolating salicylamide intermediates and alkylated salicylamides. The method is simple to perform and is amenable to industrial scale-up for commercial production.

The following examples are intended to describe the present invention without limitation. All percentages are by weight unless otherwise specified.

EXAMPLE 1

Preparation of 5-chlorosalicylamide

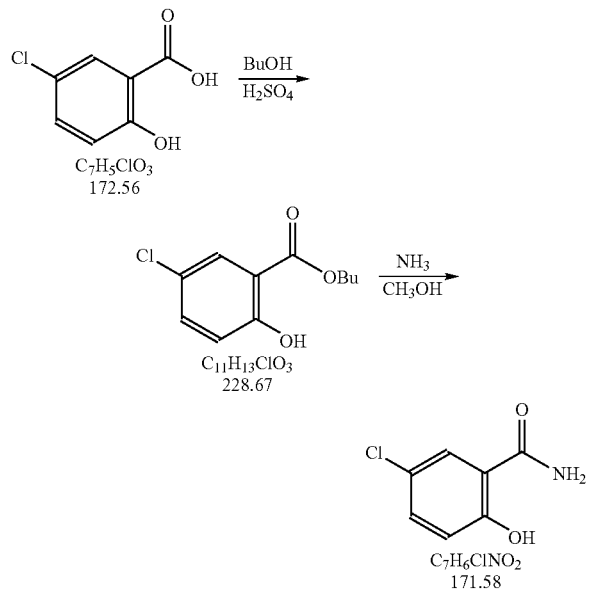

All chemicals are available from Sigma-Aldrich (Highland, Ill.). 5-chlorosalicylic acid (2000 g, 1 equiv., 11.59 moles) and reagent grade n-butanol (5000 mL, 4.7 equiv, 54.64 moles) were charged to a 12 L four neck, round bottom flask equipped with a thermocouple temperature readout, overhead stirrer, and 1 L Dean-Stark trap/reflux condenser. The Dean-Stark trap was pre-charged with an additional 1000 mL of n-butanol. The reaction set up was purged with dry nitrogen and a dry nitrogen atmosphere was maintained during the reaction.

Concentrated sulfuric acid (50 g, 0.04 equiv., 0.51 moles) was added and a heating mantle was placed on the reaction flask. The reaction was heated to reflux and maintained at reflux for about 30 hours (until >95% conversion to the ester was found by HPLC).

The heating mantle was removed and the reaction mixture allowed to cool to ambient temperature. The Dean-Stark trap was drained and removed.

1000 mL deionized water was charged to the reaction mixture, while keeping the temperature at about 28° C., and stirred for 10 minutes. The aqueous layer was allowed to settle (about 30 minutes) and was then siphoned off and discarded.

1000 mL 10 wt % sodium bicarbonate was charged and the mixture was stirred for 10 minutes. The aqueous layer was allowed to settle (about 30 minutes to one hour) and was then siphoned off and discarded.

500 mL deionized water was charged and the mixture stirred for 10 minutes. The aqueous layer was allowed to settle (about 30 minutes) and was then siphoned off and discarded. This wash was repeated with another 500 mL of deionized water. The aqueous phase was removed and discarded.

The reactor was set for atmospheric distillation into a tared 5 L receiver. Distillation was run until the pot temperature rose to between about 140 and 150° C.

The reactor was then set for vacuum distillation. The pressure was slowly lowered to 500 mm Hg. The pot temperature fell and the remaining n-butanol and n-butyl ether (a reaction byproduct) distilled off.

The heating was stopped and the reaction mixture allowed to cool to ambient temperature. The vacuum was broken. The distillate was poured into a large separatory funnel and the upper organic phase was saved for later recovery or reuse in other batches of this process.

The pot residue was cooled to about 23° C. and 8000 mL anhydrous methanol was charged.

The pot residue was vacuum filtered (Buchner funnel and WHATMAN® #1 paper (Whatman Paper Ltd., Kent, England) were wetted with n-butanol) into a 22 L, five neck flask set up with an overhead stirrer, reflux condenser, thermocouple temperature readout, gas inlet adapter, and nitrogen atmosphere.

The flask was setup with an ammonia cylinder with regulator, and an oil bubbler. The headspace of the reactor was flushed with anhydrous ammonia (about 600 g, 4 equiv., 35 moles), adding the ammonia so that the bubbler just barely bubbled. The reaction was continued approximately 18–24 hours at ambient temperature and pressure until >99% conversion by HPLC. The reactor was set for atmospheric distillation into a tared 5 L flask. About 4000 mL of the solvent was distilled off. The pot mixture formed a precipitate about half way through this distillation. The distillate was saved for reuse in other batches of this process.

The pot residue was cooled to between about 40° C. and 50° C. Deionized water (4000 mL) was slowly charged to the pot slurry. The pot slurry became thicker during this water charge.

The slurry was cooled to about 5° C. with an ice bath. The pH of the slurry was adjusted to about 4 with concentrated hydrochloric acid.

The solid product was recovered by vacuum filtration. The filter cake was washed with 2000 mL deionized water. The product was dried in a 50° C. vacuum oven with full vacuum for about 20 hours. About 1880 g of material was obtained. The yield was about 95%.

EXAMPLE 2

Preparation of
N-(5-chlorosalicyloyl)-8-aminocaprylic acid

To a clean, dry, 200 gallon glass-lined reactor, 178 L of dry acetonitrile is added. The agitator is set to 100–125 rpm and the reactor contents are cooled to about 9° C. 74 kg of 5-chloro salicylamide, available from Polycarbon Industries of Leominster, Mass., is charged to the reactor and the charging port is closed. 47 L of dry pyridine is charged to the reactor. The resulting slurry is cooled to about 9° C. Cooling is applied to the reactor condenser and valve overheads are set for total reflux. Over 2 hours, 49.7 kg of ethylchloroformate is charged to the 200 gallon reactor while maintaining the batch temperature at about 14° C. Note that ethylchloroformate can contain 0.1% phosgene and is extremely reactive with water. The reaction is highly exothermic and requires the use of a process chiller to moderate reaction temperature.

The reactor contents are agitated for 30 minutes at 10–14° C., once the ethylchloroformate addition is complete. The reactor contents are then heated to about 85° C. over 25 minutes, collecting all distillate into a receiver. The reactor contents are held at 85–94° C. for approximately 6 hours, collecting all distilled material into a receiver. The reaction mixture is sampled and the conversion (>90%) monitored by HPLC. The conversion is found to be 99.9% after 6 hours. The reactor contents are cooled to about 19° C. over a one-hour period. 134 L of deionized water is charged to the reactor. A precipitate formed immediately. The reactor contents are cooled to about 5° C. and agitated for 10.5 hours. The product continued to crystallize out of solution. The reactor slurry is centrifuged. 55 L of deionized water is charged to the 200-gallon, glass-lined reactor and the centrifuge wet cake is washed. The intermediate is dried under full vacuum (28" Hg) at 58° C. for 19.5 hours. The yield is 82.6 kg 6-chloro-2H-1,3-benzoxazine-2,4(3H)-dione. This intermediate is packaged and stored so that it is not exposed to water.

In the next preparation, absolutely no water can be tolerated in the steps up to the point where distilled water is added.

222 L of dry dimethylacetamide is charged to a dry 200 gallon glass-lined reactor. The reactor agitator is set to 100–125 rpm. Cooling is applied to the condenser and valve reactor overheads are set for distillation. 41.6 kg of dry anhydrous sodium carbonate is charged to the reactor and the reactor charging port is closed. Caution is used due to some off-gassing and a slight exothermic reaction. 77.5 kg of dry 6-chloro-2H-1,3-benzoxazine-2,4(3H)-dione is charged to the reactor. Quickly, 88 kg of dry ethyl-8-bromooctanoate is charged to the reactor. The reaction is evacuated to 22–24 inches of vacuum and the reactor temperature is raised to 65–75° C. The reactor temperature is maintained and the contents are watched for foaming. The reactor mixture is sampled and monitored for conversion by monitoring for the disappearance of the bromo ester in the reaction mixture by gas chromatography. The reaction is complete after 7 hours. The vacuum is broken and the reactor contents are cooled to 45–50° C. The contents are centrifuged and the filtrate sent into a second 200 gallon glass-lined reactor. 119 L of ethanol (200 proof denatured with 0.5% toluene) is charged to the first 200 gallon reactor, warmed to about 45° C. and the filter cake washed with warm ethanol and this wash is charged to the reaction mixture in the second 200 gallon reactor.

The agitator is started on the second 200 gallon reactor. The reactor contents are cooled to about 29° C. 120 L distilled water is slowly charged to the second reactor, with the water falling directly into the batch. The reactor contents are cooled to about 8° C. The intermediate comes out of solution and is held for 9.5 hours. The resultant slurry is centrifuged. 70 L ethanol is charged to the reactor, cooled to about 8° C., and the centrifuge cake is washed. The wet cake is unloaded into double polyethylene bags placed inside a paper lined drum. This yields ethyl 8-(6-chloro-2H-1,3-benzoxazine-2,4(3H)-dionyl)octanoate.

400 L purified water, USP and 45.4 kg sodium hydroxide pellets are charged to a 200 gallon glass-lined reactor and the agitator is set to 100–125 rpm. 123.5 kg of the ethyl 8-(6-chloro-2H-1,3-benzoxazine-2,4(3H)-dionyl)octanoate wet cake is charged to the reactor. The charging port is closed. Cooling water applied to the condenser and the valve reactor overheads are set for atmospheric distillation. The reactor contents are heated to about 98° C. and the conversion is monitored by HLPC. Initially (approximately 40 minutes) the reactor refluxes at about 68° C., however, as the ethanol is removed (over 3 hours) by distillation the reactor temperature rises to about 98° C. The starting material disappears, as determined by HPLC, at approximately 4 hours. The reactor contents are cooled to about 27° C. 150 L purified water, USP is charged to an adjacent 200 gallon glass-lined reactor and the agitator is set to 100–125 rpm. 104 L concentrated (12M) hydrochloric acid is charged to the reactor and cooled to about 24° C. The saponified reaction mixture is slowly charged (over 5 hours) to the 200 gallon glass-lined reactor. The material (45 L and 45 L) is split into 2 reactors (200 gallons each) because of carbon dioxide evolution. The product precipitated out of solution. The reaction mixture is adjusted to pH 2.0–4.0 with a 50% sodium hydroxide solution (2 L water, 2 kg sodium hydroxide). The reactor contents are cooled to about 9–15° C. The intermediate crystallizes out of solution over approximately 9 hours. The reactor slurry is centrifuged to isolate the intermediate. 50 L purified water, USP is charged to a 200 gallon glass-lined reactor and this rinse is used to wash the centrifuge wet cake. The wet cake is unloaded into double polyethylene bags placed inside a plastic drum. The N-(5-chlorosalicyloyl)-8-aminocaprylic acid is dried under vacuum (27" Hg) at 68° C. for 38 hours. The dry cake is unloaded into double polyethylene bags placed inside a 55-gallon, steel unlined, open-head drums with a desiccant bag placed on top. This yields N-(5-chlorosalicyloyl)-8-aminocaprylic acid.

All patents, publications, applications, and test methods mentioned above are hereby incorporated by reference. Many variations of the present matter will suggest themselves to those skilled in the art in light of the above detailed description. All such obvious variations are within the patented scope of the appended claims.

What is claimed is:

1. A method for preparing a salicylamide comprising the step of reacting a $C_4$ or higher alkyl ester of salicylic acid or a derivative thereof with 8-aminocaprylic acid in alcohol to yield the salicylamide.

2. A method for preparing an alkylated salicylamide comprising the steps of:
   (a) reacting a $C_4$ or higher alkyl ester of salicylic acid or a derivative thereof with at least one amine selected from the group consisting of monoalkylamines, dialkylamines, ammonia, and any combination of any of the foregoing in alcohol to yield a first salicylamide; and
   (b) alkylating the first salicylamide to form the alkylated salicylamide, wherein the alkylated salicylamide is selected from N-(5-chlorosalicyloyl)-8-aminocaprylic acid, N-(10-[2-hydroxybenzoyl]amino)decanoic acid, N-(8-[2-hydroxybenzoyl]amino)caprylic acid, or a salt thereof.

3. The method of claim 2, wherein step (b) comprises:
   (i) protecting and activating the first salicylamide to form a protected/activated salicylamide;
   (ii) alkylating the protected/activated salicylamide with an alkylating agent to form a protected/activated alkylated salicylamide; and
   (iii) deprotecting and deactivating the protected/activated alkylated salicylamide to form the alkylated salicylamide.

4. The method of claim 2, wherein the alkylated salicylamide is N-(5-chlorosalicyloyl)-8-aminocaprylic acid or a salt thereof.

5. The method of claim 2, wherein the alkylated salicylamide is N-(10-[2-hydroxybenzoyl]amino)decanoic acid or a salt thereof.

6. The method of claim 2, wherein the alkylated salicylamide is N-(8-[2-hydroxybenzoyl]amino)caprylic acid or a salt thereof.

7. A method for preparing an alkylated salicylamide comprising the steps of:
  (a) reacting salicylic acid or a derivative thereof with a $C_4$ or higher alcohol in the presence of at least one of sulfuric acid, a sulfonic acid, or a mineral acid to form a $C_4$ or higher alkyl ester of salicylic acid or a derivative thereof;
  (b) converting the $C_4$ or higher alkyl ester into a first salicylamide;
  (c) alkylating the first salicylamide to form the alkylated salicylamide; wherein the alkylated salicylamide is selected from N-(5-chlorosalicyloyl)-8-aminocaprylic acid, N-(10-[2-hydroxybenzoyl]amino)decanoic acid, N-(8-[2-hydroxybenzoyl]amino)caprylic acid, or a salt thereof.

8. The method of claim 7, wherein step (b) comprises reacting the $C_4$ or higher alkyl ester with at least one amine selected from the group consisting of monoalkylamines, dialkylamines, ammonia, and any combination of any of the foregoing in alcohol to yield the first salicylamide.

9. The method of claim 7, wherein step (c) comprises:
  (i) protecting and activating the first salicylamide to form a protected/activated salicylamide;
  (ii) alkylating the protected/activated salicylamide with an alkylating agent to form a protected/activated alkylated salicylamide; and
  (iii) deprotecting and deactivating the protected/activated alkylated salicylamide to form the alkylated salicylamide.

10. The method of claim 8, wherein the alkylated salicylamide is N-(5-chlorosalicyloyl)-8-aminocaprylic acid or a salt thereof.

11. The method of claim 8, wherein the alkylated salicylamide is N-(10-[2-hydroxybenzoyl]amino)decanoic acid or a salt thereof.

12. The method of claim 8, wherein the alkylated salicylamide is N-(8-[2-hydroxybenzoyl]amino)caprylic acid or a salt thereof.

13. The method of claim 8, wherein the alkylated salicylamide is N-(4-methoxysalicyloyl)-8-aminocaprylic acid or a salt thereof.

* * * * *